US007762975B2

(12) United States Patent
Memminger

(10) Patent No.: US 7,762,975 B2
(45) Date of Patent: Jul. 27, 2010

(54) DEVICE FOR GUIDING THE LEG DURING A HIP OPERATION, PARTICULARLY DURING AN ENDOPROSTHESIS IMPLANTATION

(75) Inventor: Michael Memminger, Bozen (IT)

(73) Assignee: Innovative Orthopedic Technologies, LLC, Houston, TX (US)

( * ) Notice: Subject to any disclaimer, the term of this patent is extended or adjusted under 35 U.S.C. 154(b) by 326 days.

(21) Appl. No.: 11/667,485

(22) PCT Filed: Nov. 9, 2005

(86) PCT No.: PCT/EP2005/055836

§ 371 (c)(1), (2), (4) Date: Oct. 31, 2007

(87) PCT Pub. No.: WO2006/051077

PCT Pub. Date: May 18, 2006

(65) Prior Publication Data

US 2008/0214976 A1 Sep. 4, 2008

(30) Foreign Application Priority Data

Nov. 10, 2004 (DE) ....................... 10 2004 054 332

(51) Int. Cl.
*A61F 5/00* (2006.01)

(52) U.S. Cl. ........................................................ 602/39

(58) Field of Classification Search .................. 602/32, 602/33, 34, 35, 36, 38, 39; 5/600, 607–608, 5/610, 621–624, 648, 650, 651; 248/348.1; 108/137, 139, 140
See application file for complete search history.

(56) References Cited

U.S. PATENT DOCUMENTS

| | | | | |
|---|---|---|---|---|
| 2,198,871 | A * | 4/1940 | Haboush | 602/39 |
| 4,509,509 | A | 4/1985 | Teasdale et al. | |
| 4,802,464 | A | 2/1989 | Deprez | |
| 5,423,682 | A | 6/1995 | Clarke et al. | |
| 5,658,315 | A | 8/1997 | Lamb et al. | |
| 6,371,897 | B1 | 4/2002 | Huang | |

FOREIGN PATENT DOCUMENTS

| | | |
|---|---|---|
| DE | 125 351 | 12/1900 |
| EP | 0 496 528 | 7/1992 |
| EP | 1 364 636 | 11/2003 |

OTHER PUBLICATIONS

Kawai Koremori, Patent Abstracts of Japan, Jun. 30, 1999, vo. 1999, No. 08 & JP 11 05688 A, Mar. 2, 1999.
International Search Report for PCT/EP2005/055836 dated Mar. 10, 2006.
German Version of International Search Report for PCT/EP2005/055836 dated Mar. 10, 2006.

* cited by examiner

*Primary Examiner*—Patricia M Bianco
*Assistant Examiner*—Tarla R Patel
(74) *Attorney, Agent, or Firm*—Conley Rose, P.C.

(57) ABSTRACT

Leg-holding traction device (57), especially for hip operations, comprising a rail (31), that contains a circular arc-shaped guide, and is rotatable about a turning axis (71) running perpendicular to the circular arc-shaped guide, and a leg holder (75) that is adjustably supported on the rail (31).

33 Claims, 11 Drawing Sheets

Figure 1:
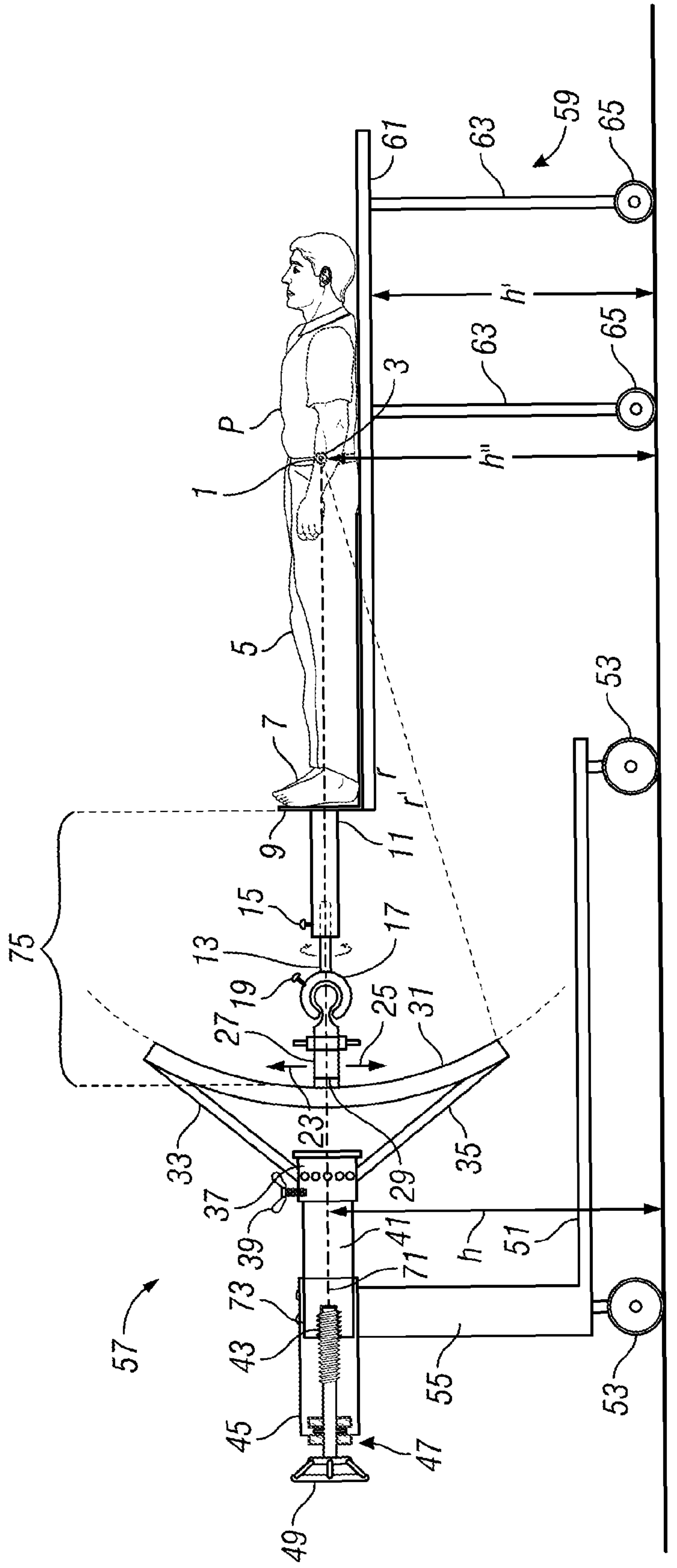

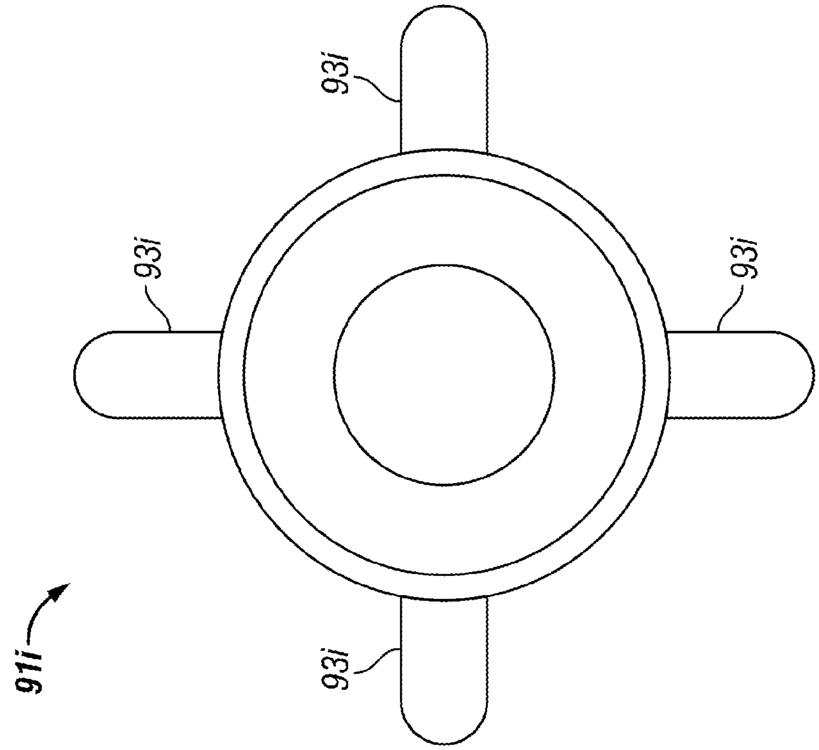
FIG. 10
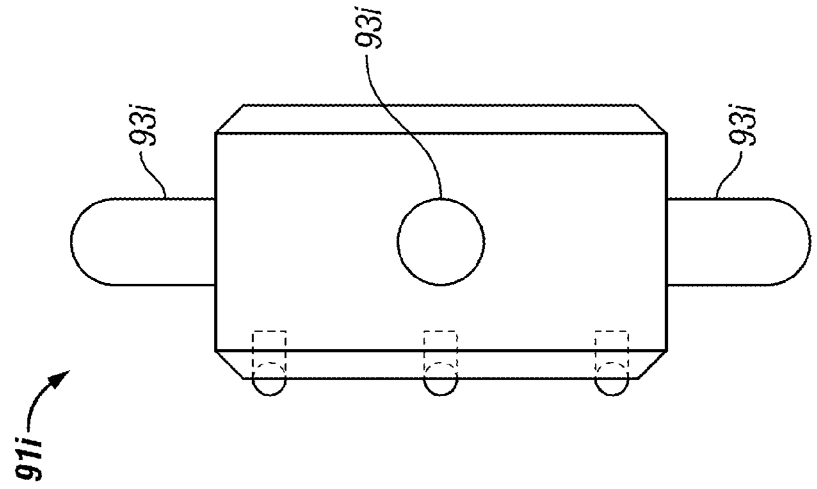

DEVICE FOR GUIDING THE LEG DURING A HIP OPERATION, PARTICULARLY DURING AN ENDOPROSTHESIS IMPLANTATION

The invention relates to an auxiliary device for an operating table for the conduct of a hip prosthesis operation, especially a leg-holding traction device.

Hip prosthesis operations or hip operations or prosthesis implantations are conducted with increasing frequency, to replace with a prosthesis a hip joint worn in the course of the life of a patient. This prosthesis is also designated as an artificial hip joint, hip joint prosthesis or hip joint total endoprosthesis. The procedure includes first the replacement of the natural joint socket of the pelvis and subsequently a replacement of the femoral head by the prosthesis portion of the femur with the capping plastic head. The latest procedures of the hip operation proceed minimally invasively, so that an operative incision to reach to the joint area is only 6 cm to 10 cm long and occurs without severing muscle or tendon tissue, so that the patient in principle can already walk again on the same day.

During the operation the patient lies on a so-called trauma bed, to which a leg extender is attached. The leg extender is a device to exert longitudinal tension on the leg and to bring the leg into certain positions (so that the operation can be conducted more simply). The hip operation proceeds in several steps delineated from each other: first the skin incision is made and then the joint socket is replaced. [-2-] Thereafter the leg of the patient is moved in a precisely defined way, so that the surgeon obtains access to the femoral head and/or the femoral neck; this precisely defined movement includes first a lowering of the leg, whereby the leg remains in a plane parallel to the sagittal plane of the body, second a rotation of the foot by about 90° toward the outside and third a drawing in respectively an adduction of the leg, so that it is turned into an area located behind the patient. Only after these movements of the leg, which is held over the entire time under a mechanical tensile stress, is a further working on the proximal femur possible. After the replacement of the joint head, the movements are run in the reverse sequence and the wound is sutured.

In this multiple difficulties arise: for one, with the traditional devices during the movement sequences mentioned above, a constant readjustment of multiple axes, especially in regard to the maintaining of a defined mechanical tensile stress, is required. If the leg would be lowered without any guidance, the tensile stress would increase to a disadvantageous degree. This necessity of stepwise, continuous lowering and readjustment prolongs the duration of the operation, depending on the degree of experience of the one who operates this device. It has been shown that hip prosthesis implantations with the assistance of the trauma bed last considerably longer if the customary trauma beds are operated by inexperienced personnel.

A further disadvantage is that a lowering of the leg can not be continued arbitrarily far downwards, because the foot of the patient otherwise bumps on the floor. A [-3-] higher placement of the patient is not possible, because thus the area of an optimal operation height is abandoned.

Known, for example, is a device from the manufacturer Maquet. With this we deal with a device that supports each of both legs of the patient and via the foot ends adjustable at an interval to the torso provides an adjustable tensile force to each of the legs of the patient. This device (bed) possesses the following disadvantages: Either the lowering of each leg is possible only stepwise in alternations with a continuous readjustment of the tensile stress, or a completely new trauma bed must be acquired, which is costly.

In U.S. Pat. No. 4,802,464 a tensioning device for operating tables and orthopedic operational devices is described, that essentially is carried out on the lower limbs of a patient under the control of a device with a radiogenic source. For this a device is proposed with sufficiently movable arms for the application of a tensile stress, whereby the control device can be used while making a free space available. The arms are swiveled on the device, whereby the joints are placed in the vicinity of the hip joint of the patient, and whereby tensional forces via tensioning devices brought into engagement with the feet of the patient are applied on the ends of the arms.

Upon operating the turning axes, in fact the tensile stress for the particular leg must be readjusted stepwise, matching the turning of the arm. This requires a very experienced operator or however a time that prolongs the operational duration to a perceptible degree and thus represents a disadvantage for the patients. Additionally, the device is a two-arm design, which additionally makes it more expensive to operate and costlier.

[-4-] It is the task of the present invention to propose a guide device that exhibits ease of manipulation and in which readjustment is possible by untrained personnel or the surgeon himself with small time expenditures.

The invention proposes a device for guidance of a leg during a hip operation according to claim 1. Additional advantages, aspects and details of the invention follow from the subordinate claims of the description and the drawings.

According to a first aspect the invention proposes a leg-holding traction device especially for hip operations comprising a rail, that includes a circular arc-type guide and is able to rotate about a turning axis running perpendicular to the circular arc-shaped guide and a leg holder that is adjustably supported on the rail.

According to a further aspect of the invention, the rail is longitudinally adjustable in the direction of the turning axis.

According to a further aspect of the invention, the leg-holding traction device contains a chassis with a mounting support for a bushing for receipt of a pistonlike component adjustable in the bushing, that supports the rail on its free end.

According to a further aspect of the invention, the adjustment direction of the pistonlike component lies in essence parallel to the turning axis.

[-5-] According to a further aspect of the invention, the adjustment direction of the pistonlike component aligns with the turning axis.

According to a further aspect of the invention, the leg-holding traction device contains a sliding device that is designed for a defined adjustment of the pistonlike component and thus also the rail in the direction of the turning axis.

According to a further aspect of the invention, the pistonlike component can be supported on rolling elements against at least one interior side of the bushing.

According to a further aspect of the invention, the pistonlike component is restrainable in the bushing.

According to a further aspect of the invention, the adjustable device is activated by turning a spindle, which spindle is placed parallel to the turning axis or in alignment with the turning axis and is freely rotatably supported in the side of the bushing opposite the open side as well as in the pistonlike component, so that a turning of the spindle causes a shifting of the pistonlike component parallel to the turning axis or along the turning axis.

According to a further aspect of the invention, a head component supported rotatably about the turning axis and supporting the turning axis is attached on the free end of the pistonlike component.

According to a further aspect of the invention, the rail is attached on the head component of the pistonlike component.

[-6-] According to a further aspect of the invention, the rail is attached on the head component of the pistonlike component using mounting pieces.

According to a further aspect of the invention, the head element is restrainable relative to a turning about the turning axis.

According to a further aspect of the invention, the pistonlike component is securely connected with the rail.

According to a further aspect of the invention, the pistonlike component is secured in essence freely in the receiving bushing, adjustably and rotatably.

According to a further aspect of the invention, the pistonlike component is equipped with an exterior threading.

According to a further aspect of the invention, an operating component is provided with an interior threading matching to the exterior threading of the pistonlike component, and controllable by a handle device.

According to a further aspect of the invention, the operating component is attached to one end of the pistonlike component, which is placed opposite the end bearing the rail, whereby the bushing carrying the pistonlike component is placed in the center.

According to a further aspect of the invention, a turning of the control element causes a displacement of the pistonlike component relative to the receiving bushing.

According to a further aspect of the invention, the pistonlike component is restrainable in the receiving bushing.

[-7-] According to a further aspect of the invention, the receiving bushing possesses a multiplicity of boreholes along a circumference taken perpendicular to the displacement direction.

According to a further aspect of the invention, the pistonlike component is restrainable in the receiving bushing against turning about the axis by possessing a longitudinal groove extending in essence over its entire length, in which a pin or a screw is placed over one of the boreholes or screwed in.

According to a further aspect of the invention, the rail at a height h, that in essence matches the height of the turning axis, contains a first circular arch-shaped area with a first curvature radius r and a second circle-shaped area at a height deviating from the height h with a second curvature radius r', whereby $r \geqq r'$ is valid.

According to a further aspect of the invention the rail is height-adjustable, to permit the surgeon an individual operational height.

According to a further aspect of the invention, the leg-holding traction device is provided with restrainable rollers, so that it is moveable on a floor.

According to a further aspect of the invention, the leg-holding traction device contains a foot securing device, which contains: a sole plane for placement of a sole of a foot, at least one attachment device secured on the sole plate, with which the foot is securely brought into contact with the sole plate, as well as a hollow spar/spar, that is attached perpendicular to the sole plate.

[-8-] According to a further aspect of the invention, the hollow spar/spar is attached on the side opposite the heel area of the foot.

According to a further aspect of the invention, the leg holder is longitudinally adjustable and the two ends of same are swivelable toward each other in the longitudinal axis.

According to a further aspect of the invention, the leg holder contains: a gliding piece on a first end of the leg holder, a foot securing device on the other end of the leg holder and a device attached between for the swiveling undertaken toward each other as well as the setting of an interval between the gliding piece and the foot securing device.

According to a further aspect of the invention, the two ends of the leg holder are swivelable toward each other by at least 90°.

According to a further aspect of the invention, the leg holder further contains: a gliding piece onto which a shaft is secured, that is linked via a joint with an inner spar, as well as a hollow spar able to slide and restrainably receive the inner spar, which is attached on the foot securing device or at least one spar on which the foot securing device is adjustable.

According to a further aspect of the invention, the sliding piece bearing the leg holder is accepted by the rail and adjustable and restrainable along same.

[-9-] According to a further aspect of the invention, the foot-securing device is attached to the end of the leg holder on the end opposite the sliding piece.

According to a further aspect of the invention, the axes of the joint are restrainable with each other.

According to a further aspect of the invention, the multi-axle joint contains a ball joint or a universal joint or two disks rotatable against each other.

According to a further aspect of the invention, the axes of the universal joint are formed by two bolts or screws placed perpendicular to each other, restrainable via levers.

According to a further aspect of the invention, the joint is formed from a head seated on the shaft, which is designed so that it secures a disk-shaped end of the inner spar rotatably, so that the inner spar is rotatable relative to the shaft on the common axis.

According to a further aspect of the invention, the joint is restrainable by means of a screw.

According to a further aspect of the invention, valid for the height h of the turning axis from the floor is: 85 cm$\leqq$h$\leqq$130 cm, whereby preferably valid is: 95 cm$\leqq$h$\leqq$120 cm.

According to a further aspect of the invention, valid for the first curvature radius is: 90 cm$\leqq$r$\leqq$260 cm, whereby preferably valid is: 100 cm$\leqq$r$\leqq$190 cm, whereby further preferably valid is: 120 cm$\leqq$r$\leqq$160 cm, whereby further preferably valid is: r=130 cm.

According to a further aspect of the invention, valid for the second curvature radius is: 80 cm$\leqq$r'$\leqq$250 cm, whereby preferably [-10-] valid is: 90 cm$\leqq$r'$\leqq$180 cm, whereby further preferably valid is: 110 cm$\leqq$r'$\leqq$150 cm, whereby further preferably valid is: r'=120 cm.

According to a further aspect of the invention, the rail extends so far that the sliding piece bearing the leg holder is adjustable so far along the rail that the leg holder can assume relative to the horizontal an angle $\alpha$ of up to 60°, whereby preferably valid is: $\alpha \leqq 50°$, whereby further preferably valid is: $\alpha = 40°$.

According to a further aspect of the invention, the sliding piece bearing the leg holder is provided with rolling pieces.

According to a further aspect of the invention, the leg holder is adjustably supported on the rail in a second rail placed perpendicular thereto.

According to a further aspect of the invention, the gliding piece bearing the leg holder is designed in a manner that it bears an additional guide rail, which is placed at an angle of 90° to the first guide rail, and which in sliding admits the end of the shaft facing the bushing.

According to a further aspect of the invention, in an area on the end facing the rail piece, the shaft possesses a threading on the shaft surface.

According to a further aspect of the invention, on the shaft, an attachment piece is rotatably attached with a matching interior threading, that effectively stands in engagement with the threading of the shaft.

[-11-] According to a further aspect of the invention, the attachment piece has handle devices and projections.

According to a further aspect of the invention, the gliding piece received in the rail is restrainable by the attachment piece being turned on the threading of the shaft so far in the direction of the rail until the shaft is securely in contact with the rail.

According to a further aspect of the invention, the attachment piece possesses four or six handle devices.

According to a further aspect of the invention, an orthopedic table arrangement for hip operations is proposed, comprising an operating table with agents for horizontal sacral securing of a patient on the one end of the table and a leg-holding traction device whereby using the leg holder the distance of the leg from the guide rail is adjustable.

According to a further aspect of the invention, the operating table is situated immovably for leg guidance.

According to a further aspect of the invention, the leg-holding traction device due to its own weight is immovable to the operating table.

According to a further aspect of the invention, the leg-holding traction device is brought by a locking device securely into contact with the operating table.

[-12-] According to a further aspect of the invention, the locking device is linked securely at one end with the leg-holding traction device and has a clamp on the other end that brings it securely in contact with an upright of the operating table using a handle.

According to a further aspect of the invention, the operating table has a height h' from the floor for which is valid: 80 cm≦h'≦130 cm, whereby preferably valid is: 90 cm≦h'≦120 cm, whereby further preferably valid is that the height h of the turning axis in essence is equal to the height h" of the hip joint.

According to a further aspect of the invention, a control device is proposed for hip operations, comprising an operating table as well a leg-holding traction device, further including at least one sensor for detection of a tensile stress on the leg of the patient as well as actuator motors suitably attached and suitable coupled with the sensor, for the automatic movement of the leg into an operation-appropriate position.

According to a further aspect of the invention, the control device for hip operations contains: at least two servomotors on the multi-axis joint for a swiveling of the foot, a servomotor on the gliding piece for the shifting of the leg holder along the rail and a servomotor on the head element for a turning of the rail, at least one tensile stress sensor at least on the foot attachment device, a program storage device, a data storage device for storage of target values for a temporal sequence of a tensile stress and of measured values, a device to admit an external storage medium or a network connection, as well as a controller that, on the basis of instructions stored in the program storage device, compares measured values of tensile [-13-] stresses with the target values and undertakes an appropriate guidance of the servomotors.

According to a further aspect of the invention, the arc-shaped leg-holding traction device can be replaced by a straight rail, if sensors and servomotors maintain a certain set tensile stress.

Figure 2:
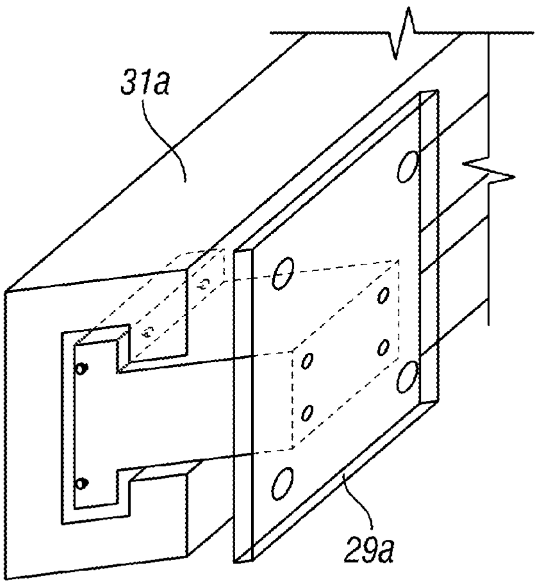
Figure 3:
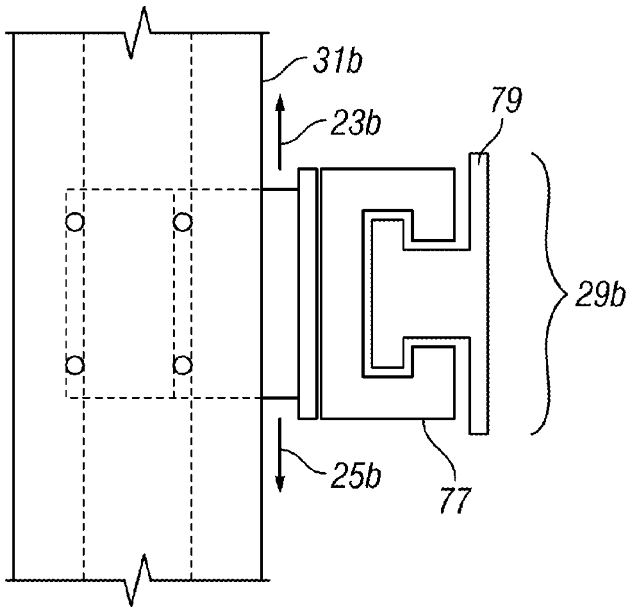
Figure 4:
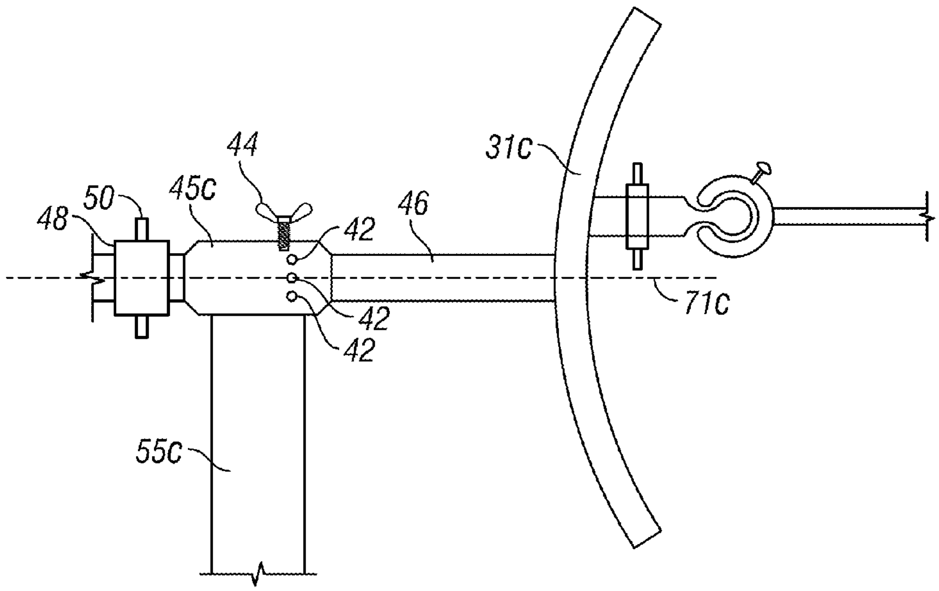
Figure 5:
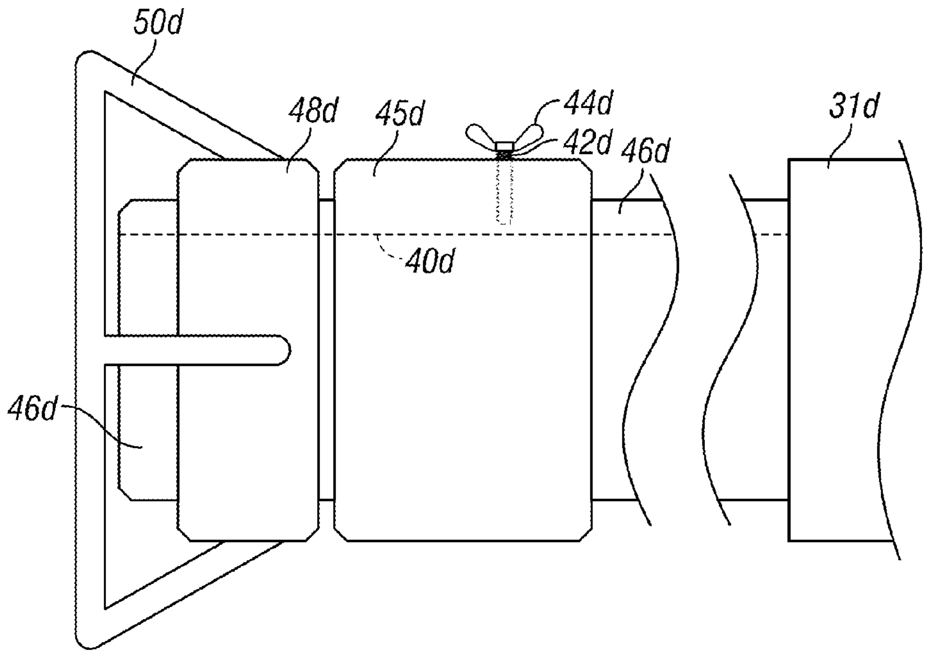
Figure 6:
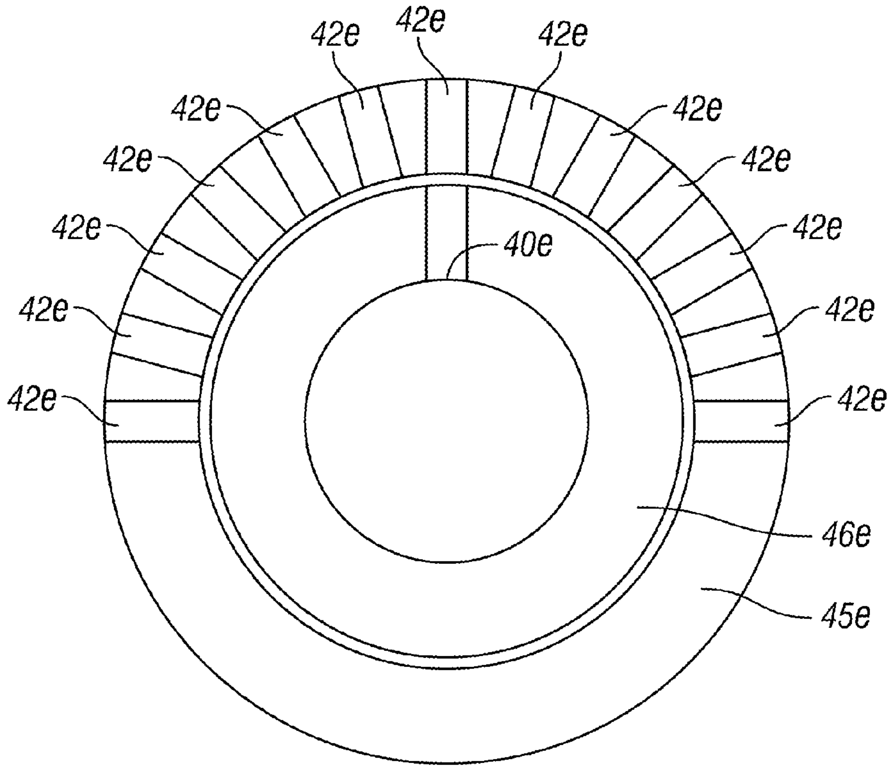
Figure 7:
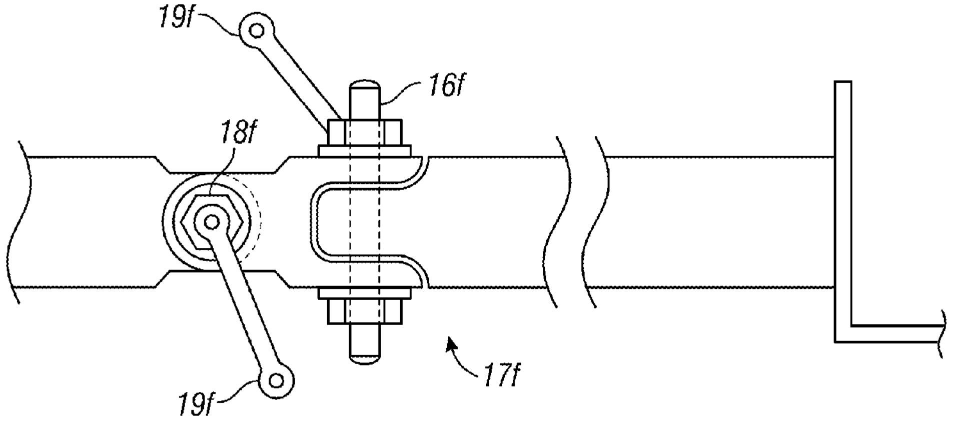
Figure 8:
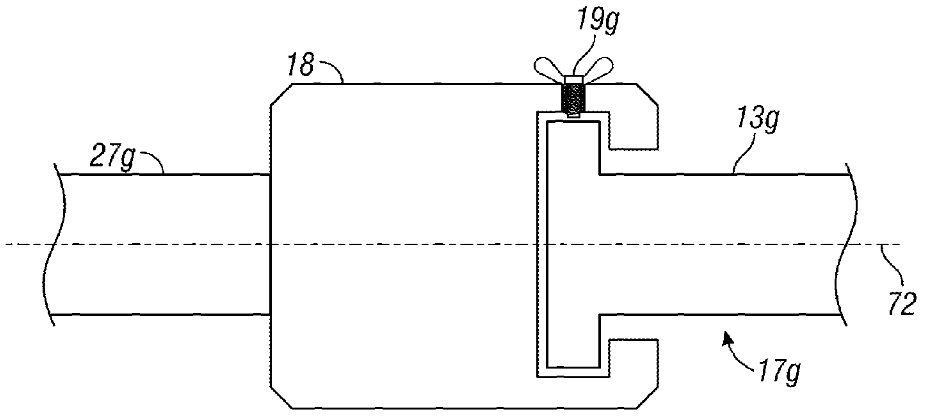
Figure 9:
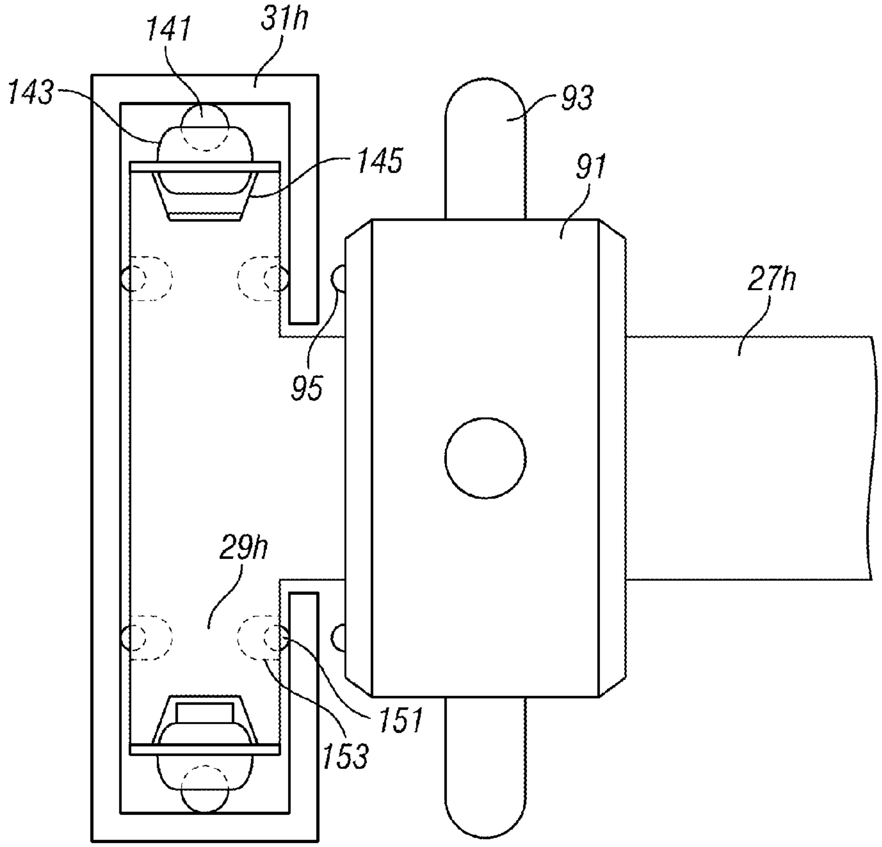
Figure 11:
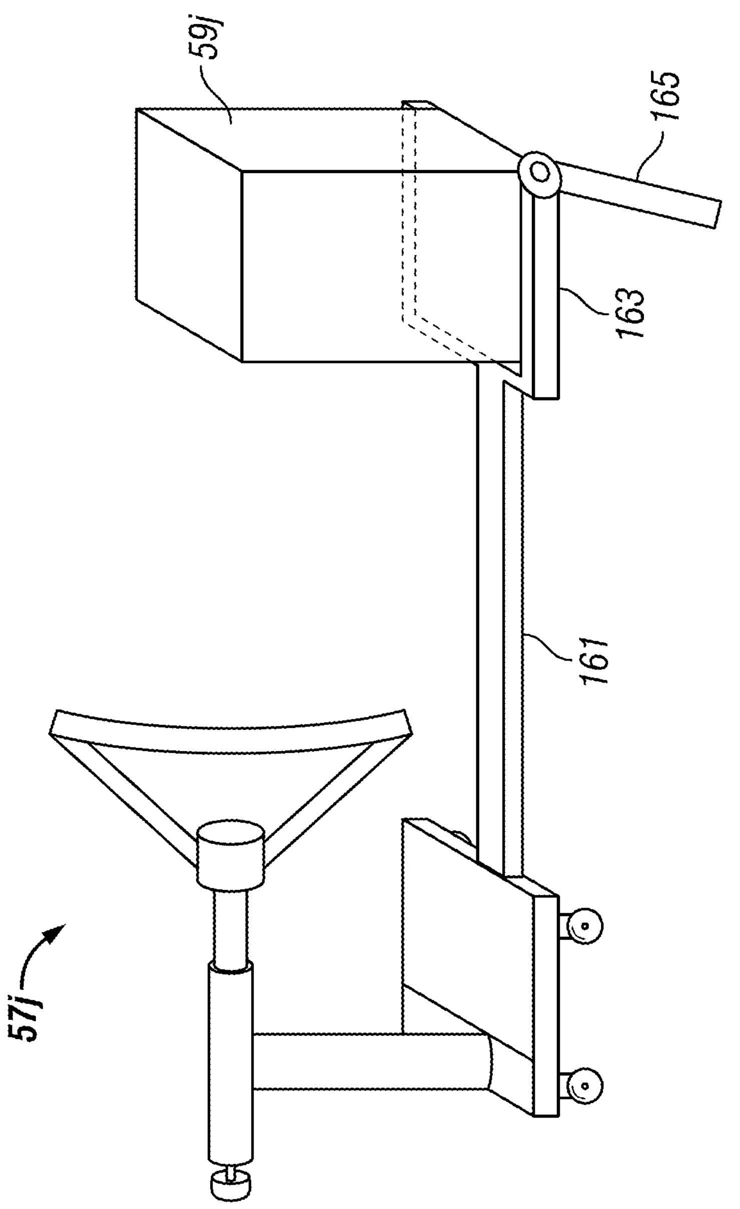
Figure 12:
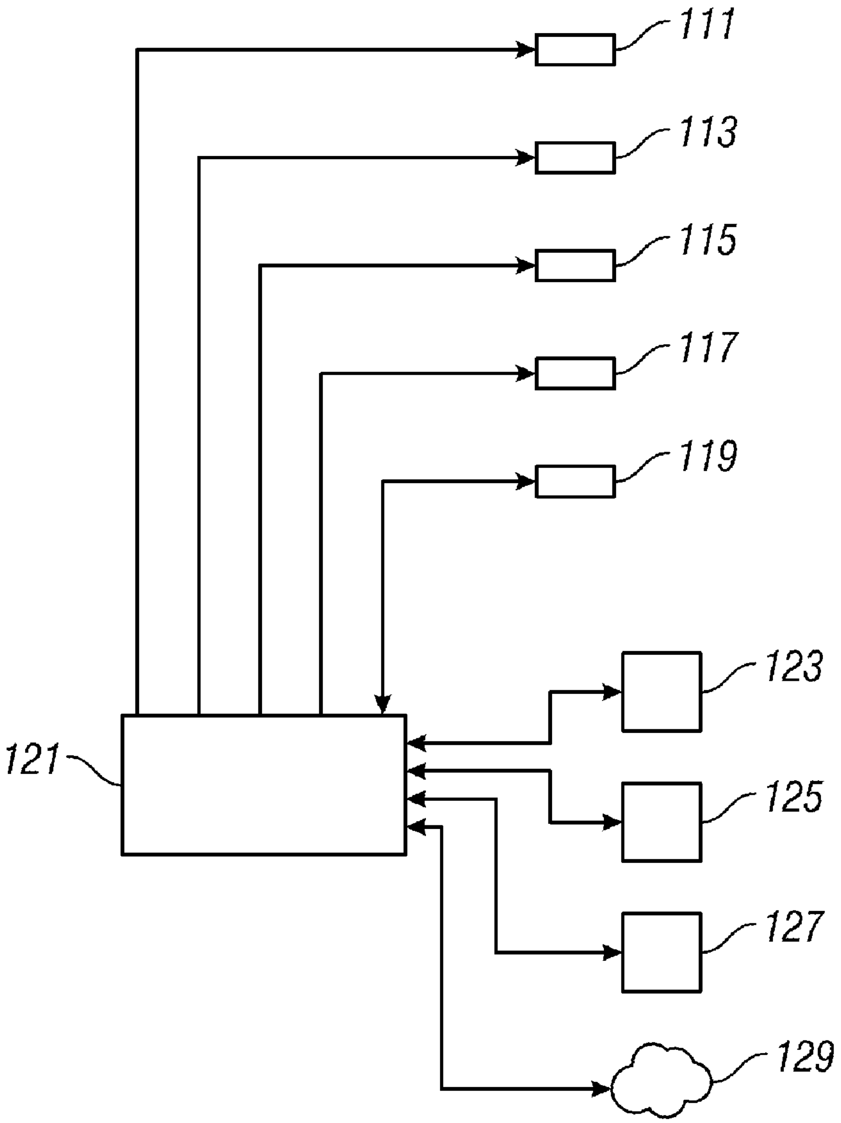

Embodiment forms of the invention are explained in greater detail subsequently using the drawings presented as follows: shown here are FIG. 1 a preferred embodiment form of the invention seen from the side;

FIG. 2 a detail of the arrangement of the sliding part accommodated in the rail in an embodiment form of the invention in a perspective front view FIG. 3 a detail of the arrangement of the sliding piece accommodated in the rail in an alternative embodiment form of the invention in a cross sectional view;

FIG. 4 a leg-holding traction device in an alternative embodiment form, in which the requisite tensile stress is applied to the leg by means of a control element;

FIG. 5 a leg-holding traction device in a schematic depiction in a side view as per FIG. 4;

FIG. 6 a detail of the embodiment form as per FIG. 4 in a schematic depiction in a front view:

[-14-] FIG. 7 a detail in an invention-specific embodiment form, that is provided with a universal joint;

FIG. 8 a detail in an invention-specific embodiment form that is provided with an alternatively designed joint;

FIG. 9 a detail in an invention-specific embodiment form, in which an arresting device secures the leg holder against the rail with a detail section of the gliding piece;

FIG. 10 an invention-specific attachment piece used;

FIG. 11 an orthopedic table arrangement for hip operations with a lock-in device, and FIG. 12 a schematically depicted invention-specific control device for hip operations.

In FIG. 1, an embodiment form of an invention-specific leg-holding traction device, especially for the use in a hip operation, is schematically depicted.

In a first preferred embodiment form, the invention-specific leg-holding traction device 57, especially for hip operations, contains a rail 31, that is a circular arc-shaped guide and is rotatable about a turning axis 71 running perpendicular to the circular arc-shaped guide and a leg holder 75 that is adjustably secured on the rail 31. Further preferred, the circular arc-shaped guide extends along the entire extent of the rail. Conditioned by this arrangement is a turning axis in the body of the patient rather that outside, through which a [-15-] movement of the leg for the operation can be guided in simple fashion; this stands in contrast to the state of the art, where the turning point of the motion lies outside the body of the patient, which makes necessary a lengthy readjustment during the motion.

The rail is longitudinally adjustable in the direction of the turning axis and height-adjustable relative to the floor. The leg-holding traction device 57 contains a chassis 55, with a securing device for a bushing 45 for admittance of a pistonlike component 41 adjustable in the bushing, that carries the rail on its free end. The adjustment direction of the pistonlike component 41 lies in essence parallel to the turning axis 71.

In a further preferred embodiment form, the adjustment direction of the pistonlike component 41 aligns with the turning axis 71

The leg-holding traction device contains a sliding device 43, 47, 49 which is designed for a defined adjustment of the pistonlike component 41 and thus also of the rail 31 in the direction of the turning axis 71.

The pistonlike component 41 may be supported on rolling elements 73 against at least one interior side of the bushing.

Suitably held spheres are preferably used as rolling elements. Also preferably used are rollers that run on roller rails placed inside the bushing 45.

The pistonlike component 41 is restrainable in the bushing 45. Preferably used for this is the adjustment device 43, 47, 49. The adjustment device 43, 47, 49 is activated via turning of a spindle 47, which spindle is placed parallel to the turning axis 71 or in alignment with the turning [-16-] axis and is secured freely rotatably in the side of the bushing opposite the open side, as well as in the pistonlike component 41 so that a turning of spindle causes an adjustment of the pistonlike component parallel to the turning axis or along the turning axis. In this the spindle is preferably turned via a manual wheel or lever. Additionally the spindle is held freely rotatably in an axle box 47 of bushing 45 and the end of the spindle is accommodated in a threaded area 43 of pistonlike component 41. In a further embodiment form, the spindle drive is attached at a height different from the height of the turning axis.

At the free end of pistonlike component 41 a head element 37, supported rotatably about the turning axis and carrying the rail, is attached. Further preferred, the head element is restrainable via a screwing device or inserting device 39. The rail 31 is attached onto the head element 37 of the pistonlike component.

The rail 31 is attached to the head element 37 of the pistonlike component 41 via retaining elements 33, 35. Preferably used as retaining elements are two braces 33, 35. Also preferably the rail is directly attached via a disklike spacer piece directly onto the head element. The head element 37 is restrainable relative to a rotation about the turning axis 71.

In an alternative embodiment form, shown in FIG. 4, the pistonlike component 46 is solidly connected with the rail 31*c*, for example it is designed as a continuous piece that has a piston area and a rail area. The pistonlike component 46 in this embodiment form is in essence freely adjustable in the receiving bushing 45*c* and rotatably supported, and it is provided with an exterior threading. An operating [-17-] piece 48 is provided with an interior threading marching to the exterior threading of the pistonlike component, and operable via a handle device 50.

The operating piece is attached on one end of pistonlike component 46, which is placed opposite the end bearing the rail 31*c*, whereby the bushing 45*c* carrying the pistonlike component is placed in the middle. A turning of the operating piece 48 causes a shift of pistonlike component 46 relative to receiving bushing 45*c*. The functional mode here is as with screws and threaded nuts standing in contact with one another: in turning the screw, its relative position to the threaded nut changes in an axial direction. To configure the design as simple as possible, here an opposed support point was dispensed with. An opposed support point is not at all necessary here, because the counterforce required to prevent that the attachment piece plus pistonlike component can freely move back and forth, is applied via the leg of the patient respectively via the tensile stress conducted through the leg. The force applied via the leg of the patient is sufficiently great to attain a sufficiently secure hold.

The pistonlike element 46 is restrainable in the receiving bushing 45*c*. The receiving bushing 45*c* has a multitude of boreholes 42 along a circumference taken perpendicular to the adjustment direction. The pistonlike component 46 is restrainable in the receiving bushing 45*c* against a turning about the axis 71*c* by its having a longitudinal groove extending in essence over its entire length, into which a pin or a screw can be inserted or screwed in via one of the boreholes 42. FIG. 4 shows this in schematic overview: On the pillar 55*c*, the bushing 45*c* is attached in the alternative [-18-] embodiment form. This bushing has a smooth, threading-free interior diameter, so that the pistonlike component 46 provided with an exterior threading is freely rotatable and adjustable in the bushing. The functional mode here is as with the threaded nut-screw connection, in which a turning of the screw causes a motion relative to the threaded nut in an axial direction. An operation of the control element via turning in a clockwise position, viewed from the side opposite the patient, causes the pistonlike component to be moved away from the patient and thus a tensile stress is built up in the leg. The rail 31*c* is rotatable about the axis 71*c*, whereby a restraining is achieved via the combination of the nut present in the pistonlike component 46 with the screw or the pin 44 with the diametric holes 42. The diametric holes 42 are placed at appropriate intervals and make possible a restraining of the rail against a turning in a multiplicity of settings.

FIG. 5 shows this interlocking in a side view: by the pin or the screw penetrating through the bushing 45*d* down to a groove depth 40*d* in the pistonlike component 46*d*, an unintended turning of pistonlike component 46*d* and thus also an unintended turning of rail 31*d* is stopped.

FIG. 6 shows this once again in a front view: the pistonlike component 46*e* has a groove with a groove depth 40*e*; the possible settings of the pistonlike component and thus of the rail (not shown here) are defined through the arrangement of diametric holes 42*e*.

[-19-] At a height h, that in essence matches the height of turning axis 71, the rail has a first circular arc-shaped area with a first curvature radius r and, at a height deviating from the height h, a second circular-shaped area with a second curvature radius r', whereby $r \leqq r'$ is valid. The areas of differing curvature radii vary constantly to each other, so that the movement of the gliding piece along the rail occurs smoothly and without abrupt changes. Owing to the condition $r>r'$, it is ensured that the leg of the patient stands under a lesser tensile stress than the initial tensile stress after the lowering. In this way, an excessive loading of the tissues is prevented and the operation facilitated. For this the gliding piece is so designed that it runs easily on the guide rail. In a preferred embodiment form it is designed with roller elements, as for example spheres. Likewise a gliding within a rail guide is preferably carried out. Further preferred, the rail is designed in a U profile, within which the sliding piece glides along on the guide rail. Additionally the sliding piece can be restrained on the rail 31.

To facilitate a shifting of the sliding piece on the rail, additionally a kind of toothed wheel can be attached on the sliding piece or the rail; the turning of a lever with wheel shifts the sliding piece on the rail toward above or below.

The invention-specific leg-holding traction device can be provided with restrainable rollers 53, so that it is movable on a floor. The rollers attached on the base plate 51 of chassis 55 are replaceable in an embodiment form by elements that stand securely in engagement with the floor, to hold a great weight of the leg-holding traction device in a special embodiment form. [-20-] Additionally the invention-specific leg-holding traction device 57 contains a foot attachment device 9, whereby the foot attachment device contains: a sole plate for placement of a sole of a foot 7, at least one attachment device connected to the sole plate, with which the foot is brought securely into engagement with the sole plate, as well as a hollow spar 11 (or at least 1 spar), that is attached perpendicular to the sole plate. Preferably the sole plate is equipped with straps, so that the foot 7 of patient P after an attachment as with sandals stands securely in engagement with the sole plate and thus with the leg-holding traction device 57. In a different embodiment form, the foot attachment device 7, 9 is embodied as a complete shoe.

The hollow spar 11 (or spar) is attached on the site opposite the heel area of the foot. In this way it is ensured that the swiveling of foot holder 75 leads to a swiveling of leg 5, whereby both swiveling axes align with each other.

The leg holder 75 is longitudinally adjustable and the two ends of same are swivelable toward each other in the longitudinal axis. Additionally, the leg holder 75 contains: a sliding piece 29; 29*a*; 29*b* on a first end of the leg holder, a foot attachment device 9 on the other end of the leg holder and a device attached between for the swiveling undertaken toward each other as well as setting of an interval between the sliding piece and the foot attachment device. An example for the receipt of a sliding piece 29*a* into a rail 31*a* is shown in FIG. 2: The cross section of the rail has a U shape with ends bent toward inwards, so that the sliding piece can not fall out. As here only indicated and described further below in detail, the sliding piece has spheres stored, so that a gliding is facilitated.

[-21-] In this the two ends of leg holder 75 are swivelable toward each other by at least 90°. Further, leg holder 75 contains: a sliding piece 29; 29*a*; 29*b*, on which a shaft 27 is attached, that is connected via a joint 17 with an interior spar 13, as well as a hollow spar 11 that receives the inner spar adjustably and restrainably, which is attached on the foot attachment device 9. The sliding piece 29 carrying the leg holder 75 is admitted by the rail and adjustable and restrainable along same. On the end opposite the sliding piece 29 of leg holder 75, the foot attachment device 9 is attached. The axes of joint 17 are restrainable by each other. Instead of a hollow spar and inner spar for setting of an exactly defined interval between rail and leg holder, also at least 2 spars can be used, that allow themselves to be adjusted toward each other via an intermediate piece or in a further version the leg holder can be adjusted directly on one (or several) spar.

The joint 17 contains a ball joint or 2 disks rotatable toward each other or a universal joint. In the latter case the axes of the universal joint 17 are formed via two bolts or screws placed perpendicular to each other, restrainable via levers 19*f*. FIG. 7 shows a detail of the embodiment form designed with a universal joint 17*f*. Here the two axes of the universal joint 16*f* and 18*f* on the projecting ends are in engagement with threaded nuts so that with assistance of two levers 19*f*, the universal joint is securely restrainable for both swiveling directions.

In an alternative embodiment for the joint 17*g* is formed from a head 18 seated on the shaft 27*g*, [-22-] that is designed so that it rotatably haltert a disk-shaped end of inner spar 13*g*, so that the inner spar 13*g* is rotatable relative to the shaft 27*g* on the common axis 72, as is illustrated in FIG. 8.

The dimensions of the leg-holding traction device result from the anatomical particulars of the person, whereby the fixed dimensions are independent of individual shapes; rather for the fixed dimensions a normal patient is assumed—the individual adaptation is each achieved by operating the described joints. For the height h of turning axis 71 from the floor, 85 cm≦h≦130 cm is valid, whereby preferably valid is: 95 cm≦h≦120 cm. For the first curvature radius: 90 cm≦r≦260 cm is valid, whereby preferably valid is: 100 cm≦r≦190 cm, whereby further preferably valid is: 120 cm≦r≦160 cm, whereby further preferably valid is: r=130 cm. Valid for the second curvature radius is: 80 cm≦r'≦250 cm, whereby preferably valid is: 90 cm≦r'≦180 cm, whereby further preferably valid is: 110 cm≦r'≦150 cm, whereby further preferably valid is: r'=120 cm. The rail extends so far that the sliding piece bearing the leg holder is adjustable so far along the rail that the leg holder can assume relative to the horizontal an angle α of up to 60°, whereby preferably valid is: α≦50°, whereby further preferably valid is: α=40°.

Further, the sliding piece 29*a* carrying the leg holder 75 is provided with rolling elements. The rolling elements can be designed as spheres enclosed via annular springs in grooves of the sliding piece, to facilitate the gliding. FIG. 9 shows an example for this: The sliding piece 29*h* accommodated into the rail 31*h* has spheres 141 on the inner friction surface with the sliding rail, which each are accommodated in [-23-] a bushing of elastic material 143, which each are fitted in a recess 145 of the sliding piece.

In a further preferred embodiment form, the leg holder is adjustably supported on the rail in a second rail placed perpendicular to this. Here the sliding piece 29*b* carrying the leg holder 75 is designed in a manner that it carries a further guide rail 77, which is placed at an angle of 90° to the first guide rail and that, sliding, accommodates the end facing the bushing 45 of shaft 27. FIG. 3 illustrates this arrangement. The rail 31*b* accommodates the gliding piece 29*b*, so that it is adjustable in the directions 23*b* and 25*b*. In the middle piece the sliding piece 29*b* contains a second guide rail 77 placed at an angle of 90° to rail 31*b*. In this, a support piece 79 is accommodated to slide, on which the end of leg holder 75 facing the bushing 45 is attached. In this way, additionally, still another prescribed motion is possible, turned by 90° relative to the sliding on the rail 31. this can be advantageous for a fine adjustment of the leg position and placement.

In one area on the end facing the rail part 31*h*, the shaft 27*h* has a threading on the shaft surface. On the shaft 27*h* an attachment piece 91 is rotatably attached with an appropriately fitting interior threading, that effectively is in engagement with the threading of the shaft. The attachment piece 91 has handle devices 93 and projections 95. The sliding piece 29*h* accommodated in the rail 31*h* is restrainable in that the attachment piece 91 is turned on the threading of shaft 27*h* as far in the direction of rail 31*h*, until the shaft, due to a static friction of the projections 95 against the rail stands securely in engagement with the [-24-] rail 31*h*. This is illustrated in FIG. 9: On the end of the leg holder adjacent to rail 31*h*, in an appropriate area, the shaft 27*h* has a threading on the exterior surface, so that the attachment piece can be turned on the screw like a threaded nut. If the attachment piece is rotated in a clockwise direction, then it ever more approaches the slide rail, until the projections 95 to due static friction no longer permit a further turning. Thus also the movement of the sliding of the sliding element is then stopped.

The attachment piece 91*i* has four or six handle devices 93*i*. This is illustrated in FIG. 10 in a side view and a front view, whereby here merely an embodiment form with four handle devices is shown. The handle devices serve for facilitated operability of the attachment piece.

In a further embodiment the attachment piece is restrained on the rail by a type of clamping jaw, which is compressed onto the rail by springs.

In a further preferred embodiment form an orthopedic table arrangement 57, 59 for hip operations is provided, comprising an operating table 59 with means 61 for horizontal sacral fixing of a patient P on the one end of the table and a leg-holding traction device 57, whereby via the leg holder 75 the interval of the leg 5 from the guide rail 31 is adjustable.

Here the operating table 59 of the orthopedic table arrangement is arranged immovable to the leg-holding traction device 57. Due to its own weight or based on a screw connection with the floor, the leg-holding traction device is immovable to the operating table. Additionally or alternatively in a further embodiment form, as shown in FIG. 11, the [-25-]

leg-holding traction device **57*j* is brought securely into engagement with the operating table 59*j* via a lock-in device. Here the lock-in device 161 is attached securely at one end with the leg-holding traction device and on the other end has a clamp 163, that securely brings into engagement an upright of the operating table via a handle 165. The operating table 59 of the orthopedic table arrangement has a height h' from the floor, for which 80 cm≦h'≦130 is valid, whereby preferably: 90 cm≦h'≦120 cm is valid, whereby additionally preferably valid is that the height h of the turning axis in essence is equal to the height h" of the hip joint 1, 3**.

The invention-specific embodiment forms permit facilitated conducting of a hip operation as versus the state of the art. Especially for the steps of the operation, in which a movement of body parts of the patient is required (lowering of the leg, swiveling of the foot as well as adduction of the leg) due to the invention-specific embodiment forms oriented to the human joints, only each simple adjustment or swiveling motions are required, so that a substantial facilitation of handling and this a speedy operation is possible even with less experienced operating personnel.

In a further embodiment form, the motion of the three steps (lowering of the leg, swiveling of the foot as well as adduction of the leg) occurs automatically through a guidance that includes: servomotors with angular sensors, sensor for measuring a tensile stress in the foot attachment device, program storage units for the running of the motors with taking into account of the assumed measurement values, data storage devices for the presetting of a time- and angle-dependent target sequence for the tensile stress.

Additionally a control device for hip operations is proposed, comprising an operating table [-26-] as well as a leg-holding traction device 57, further including at least one sensor for detecting a tensile stress on the leg of the patient as well as servomotors suitably attached and suitably coupled with the sensor for the automatic motion of the leg into an operation-appropriate position.

The control device for hip operations includes: at least two servomotors 111, 113 on the multi-axle joint 17 for a swiveling of the foot 7, a servomotor 115 on the sliding piece 29 for the adjustment of the leg holder 75 along the rail and a servomotor 117 on the head element 37 for a rotation of the rail 31, at least one tensile stress sensor 119 at least on the foot attachment device, a program storage device 123, a data storage device 125 for storage of target values for a temporal sequence of a tensile stress and of measured values, a device for receipt of an external storage medium 127 or a network connection 129, as well as a controller 121, which, on the basis of instructions stored in the program storage device 123, compares measured values of tensile stresses with the target values and undertakes an appropriate guidance of the servomotors 111, 113, 115, 117.

The invention claimed is:

1. A leg-holding traction device for orthopedic operations, especially for hip operations, comprising:

an arc-shaped guide rail having a first end and a second end;

wherein the arc-shaped guide rail is rotatable about a turning axis that is perpendicular to the circular arc-shaped guide rail; and a leg holder extending from the arc-shaped guide rail;

wherein the leg holder has a first end directly attached to the arc-shaped guide rail and positioned between the first end and the second end of the arc-shaped guide rail;

wherein the position of the first end of the leg holder along the arc-shaped guide rail is adjustable;

wherein the arc-shaped guide rail is longitudinally adjustable in a direction parallel to the turning axis.

2. The leg-holding traction device according to claim 1, further comprising a chassis including a mounting support;

wherein the mounting support includes a bushing having an open end that receives a piston-like component adjustable relative to the bushing along the turning axis;

wherein the piston-like component has a free end distal the bushing that supports the arc-shaped guide rail.

3. The leg-holding traction device according to claim 2, comprising a sliding device adapted to adjust the piston-like component and the arc-shaped guide rail in the direction of the turning axis.

4. The leg-holding traction device according to claim 3, wherein the sliding device is activated by turning a spindle, the spindle being oriented parallel to the turning axis or in alignment with the turning axis;

wherein the spindle is rotatably supported in an end of the bushing opposite the open end;

wherein the spindle is coupled to the piston-like component so that a turning of the spindle causes a shifting of the piston-like component parallel to the turning axis or along the turning axis.

5. The leg-holding traction device according to claim 2, further comprising a head component rotatably attached on the free end of the piston-like component;

wherein the arc-shaped guide rail is coupled to the head component with mounting pieces; and wherein the head component is restrainably rotatably about the turning axis.

6. The leg-holding traction device according to claim 2, wherein the piston-like component is longitudinally adjustably and rotatably adjustable relative to the bushing.

7. The leg-holding traction device according to claim 6, wherein the piston-like component includes exterior threads and an operating component including interior threads is threadingly disposed about the piston-like component; and wherein the operating component is controllable by a handle device positioned opposite the free end of the piston-like component;

wherein the bushing is positioned between the operating component and the arc-shaped guide rail.

8. The leg-holding traction device according to claim 7, wherein a turning of the operating component causes a displacement of the piston-like component relative to the bushing and wherein the piston-like component is restrainable to the bushing and restrainable against turning about the axis by a pin or screw placed or screwed in through boreholes in the bushing into a longitudinal groove extending over the entire length of the piston-like component.

9. The leg-holding traction device according to claim 1, whereby at a first height h that is substantially equal to the height of the turning axis, the rail defines a first circular arch-shaped area with a first curvature radius r and a second circle-shaped area at a second height deviating from the first height h with a second curvature radius r', whereby r≧r' is valid.

10. The leg-holding traction device according to claim 9, wherein the first curvature radius r is 90 cm≦r≦260 cm and the second curvature radius r' is 80 cm≦r'≦250 cm.

11. The leg-holding traction device according to claim 9 wherein the first curvature radius r is 100 cm≦r≦190 cm and the second curvature radius r' is 90 cm≦r'≦180 cm.

12. The leg-holding traction device according to claim 9 wherein the first curvature radius r is 120 cm≦r≦160 cm and the second curvature radius r' is 110 cm≦r'≦150 cm.

13. The leg-holding traction device according to claim 9 wherein the first curvature radius r is 130 cm and the second curvature radius r' is 120 cm.

14. The leg-holding traction device according to claim 1, further comprising at least one restrainable roller, so that it is moveable on a floor.

15. The leg-holding traction device according to claim 1, further comprising a foot securing device including:

a sole plate for placement of a sole of a foot;

at least one attachment device secured on the sole plate, with which the foot is securely brought into contact with the sole plate; and a hollow spar that is attached to the sole plate or a mounting adjustable on at least one spar;

wherein the hollow spar or the mounting adjustable on at least one spar is attached on the side opposite the heel area of the foot.

16. The leg-holding traction device according to claim 1, wherein the leg holder is longitudinally adjustable and two ends of the leg holder are swivelable toward each other in a longitudinal axis.

17. The leg-holding traction device according to claim 1, wherein the leg holder includes:

a gliding piece on a first end of the leg holder;

a foot securing device on the other end of the leg holder; and a device attached between the gliding piece and the foot securing device for swiveling and rotating toward each other and for setting of an interval between the gliding piece and the foot securing device.

18. The leg-holding traction device according to claim 17, wherein the leg holder further includes:

a shaft secured to the gliding piece, wherein the shaft is linked via a joint with an inner spar; and a hollow spar that slidably and restrainably receives the inner spar, the inner spar being attached on the foot securing device.

19. The leg-holding traction device according to claim 18, wherein the joint is selected from the group consisting of:

a restrainable joint;

two disks restrainable by pins; and a restrainable universal joint;

wherein the joint is located between the gliding piece and the foot securing device such that the foot securing device is rotatable relative to the gliding piece.

20. The leg-holding traction device according to claim 18, wherein the joint is formed from a head seated on the shaft, wherein the head rotatably receives a disk-shaped end of the inner spar such that the inner spar is rotatable relative to the shaft on a common axis.

21. The leg-holding traction device according to claim 18, wherein in an area on the end of the shaft facing the rail piece, the shaft possesses a threading on the shaft surface, to which an attachment piece is rotatably attached with a matching interior threading so that the shaft is restrainable against the rail piece by the attachment piece being turned.

22. The leg-holding traction device according to claim 17, wherein the gliding piece bearing the leg holder is adapted to be positioned along the rail such that the leg is oriented at an angle $\alpha$ of up to 60° relative to horizontal.

23. Leg-holding traction device according to claim 17, wherein the gliding piece bearing the leg holder is provided with rolling elements positioned between the gliding piece and the rail.

24. The leg-holding traction device according to claim 17, wherein the gliding piece is restrained by means of clamping jaws or pins on the arc-shaped guide rail.

25. The leg-holding traction device according to claim 1, wherein the two ends of the leg holder are swivelable toward each other in at least one plane by at least 90°.

26. The leg-holding traction device according to claim 1, wherein the turning axis is disposed at a height h from the floor that is 85 cm≦h≦130 cm.

27. An orthopedic table arrangement for hip operations, comprising:

an operating table with means for horizontal sacral securing of a patient on one end of the table; and a leg-holding traction device according to claim 1, whereby the distance of the leg from the arc-shaped guide rail is adjustable.

28. The orthopedic table arrangement according to claim 27, further comprising a height-adjustable rail.

29. The leg-holding traction device according to claim 1 wherein the turning axis is disposed at a height h from the floor that is 95 cm≦h≦120 cm.

30. The leg-holding traction device according to claim 1 wherein the arc-shaped guide rail is circular.

31. The leg-holding traction device according to claim 1 wherein the arc-shaped guide rail is directly connected to an operating table by at least one bar.

32. A control device for hip operations, comprising:

an operating table;

a leg-holding traction device comprising:

an arc-shaped guide rail that is rotatable about a turning axis that is perpendicular to the circular arc-shaped guide rail; and a leg holder that is adjustably supported on the arc-shaped guide rail;

at least one sensor for detection of a tensile stress on the leg of the patient; and a plurality of actuator motors coupled to the sensor and adapted to automatically move the leg into an operation appropriate position.

33. The control device for hip operations according to claim 32, comprising: at least two servomotors on the multi-axis joint for a swiveling of the foot, a servomotor on a gliding piece for the shifting of the leg holder along the rail and a servomotor on the head element for a turning of the arc-shaped guide rail, at least one tensile stress sensor on a foot attachment device, a program storage device, a data storage device for storage of target values for a temporal sequence of a tensile stress and of measured values, a device to admit an external storage medium or a network connection, and a controller that, on the basis of instructions stored in the program storage device, compares measured values of tensile stresses with the target values and undertakes an appropriate guidance of the servomotors.

* * * * *